US010151529B2

(12) United States Patent
Botas et al.

(10) Patent No.: US 10,151,529 B2
(45) Date of Patent: Dec. 11, 2018

(54) DYNAMIC SUSPENSION DRYING (DSD) TO CONTROL OSTWALD RIPENING

(71) Applicant: HOVIONE INTERNATIONAL LTD, Wanchai, Hong Kong (CN)

(72) Inventors: Joaquim Pedro Botas, Moita (PT); David Goncalves, Loures (PT); David Martins, Charneca de Caparica (PT); Filipe Neves, Lisboa (PT); Jose Melo, Odivelas (PT); Nuno Almeida, Porto Salvo (PT)

(73) Assignee: Hovione International LTD, Wanchai (HK)

( * ) Notice: Subject to any disclaimer, the term of this patent is extended or adjusted under 35 U.S.C. 154(b) by 231 days.

(21) Appl. No.: 14/760,095

(22) PCT Filed: Jan. 9, 2014

(86) PCT No.: PCT/GB2014/050055
§ 371 (c)(1),
(2) Date: Jul. 9, 2015

(87) PCT Pub. No.: WO2014/108687
PCT Pub. Date: Jul. 17, 2014

(65) Prior Publication Data
US 2015/0354891 A1 Dec. 10, 2015

(30) Foreign Application Priority Data
Jan. 9, 2013 (PT) .......................... 106738

(51) Int. Cl.
| *A61K 9/16* | (2006.01) |
| *F26B 3/10* | (2006.01) |
| *F26B 1/00* | (2006.01) |
| *A61K 31/58* | (2006.01) |
| *F26B 3/12* | (2006.01) |

(52) U.S. Cl.
CPC .............. *F26B 3/10* (2013.01); *A61K 9/1682* (2013.01); *A61K 9/1688* (2013.01); *A61K 31/58* (2013.01); *F26B 1/00* (2013.01); *F26B 3/12* (2013.01)

(58) Field of Classification Search
None
See application file for complete search history.

(56) References Cited

U.S. PATENT DOCUMENTS

| 4,826,689 | A | 5/1989 | Violante et al. |
| 4,997,454 | A | 3/1991 | Violante et al. |
| 6,318,649 | B1* | 11/2001 | Mazurkiewicz ........ B02C 19/06 241/152.2 |
| 6,749,868 | B1 | 6/2004 | Desai et al. |
| 2005/0009908 | A1 | 1/2005 | Hedberg et al. |
| 2013/0203717 | A1* | 8/2013 | Gil ....................... A61K 9/0075 514/172 |

FOREIGN PATENT DOCUMENTS

| WO | WO 98/14174 | 4/1998 |
| WO | WO 01 /80828 | 11/2001 |
| WO | WO 01/80828 A2 | 11/2001 |
| WO | WO 02/04125 | 1/2002 |
| WO | WO 02/04125 A2 | 1/2002 |
| WO | WO 2004/052567 | 6/2004 |
| WO | WO 2004/052567 A2 | 6/2004 |
| WO | WO 2008/013785 A2 | 1/2008 |
| WO | WO 2011/131947 | 10/2011 |
| WO | WO 2011/131947 A2 | 10/2011 |

OTHER PUBLICATIONS

Website discussing Bernoulli's Equation; (http://hyperphysics.phy-astr.gsu.edu/hbase/pber.html); downloaded Jul. 25, 2017.*
Examination Report for European Patent Application No. 14701124.1 prepared by the European Patent Office dated Jun. 13, 2017. (4 pages).
International Search Report and Written Opinion of the International Searching Authority for PCT/GB2014/050055 prepared by the European Patent Office dated Feb. 20, 2014 (8 pages).
Office Action for Chinese Patent Application No. 2014800111125 prepared by the Chinese Patent Office dated Oct. 16, 2017 and English translation thereof. (18 pages).

* cited by examiner

*Primary Examiner* — Jeffrey T. Palenik
(74) *Attorney, Agent, or Firm* — Haynes and Boone, LLP

(57) ABSTRACT

The present invention relates to a process for the control of Ostwald Ripening phenomenon occurring in particle suspensions without the need for addition of stabilizing agents, by using high pressure homogenization at mild conditions in a way that no increase or decrease in particle size occurs, thus allowing the stabilization of the suspension during the isolation step in the form of a dried powder.

15 Claims, 4 Drawing Sheets

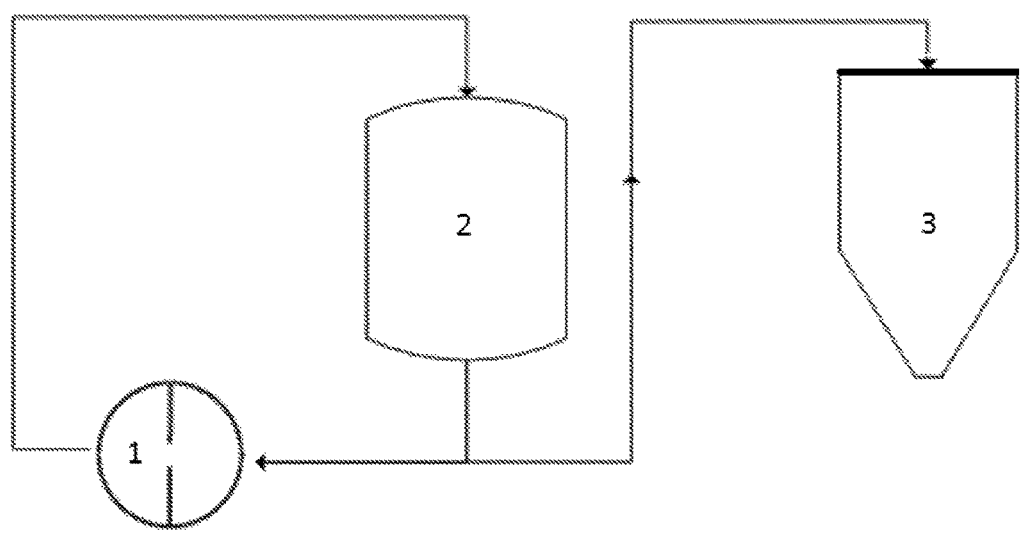
Figure 1 - Dynamic Suspension Drying Schematics

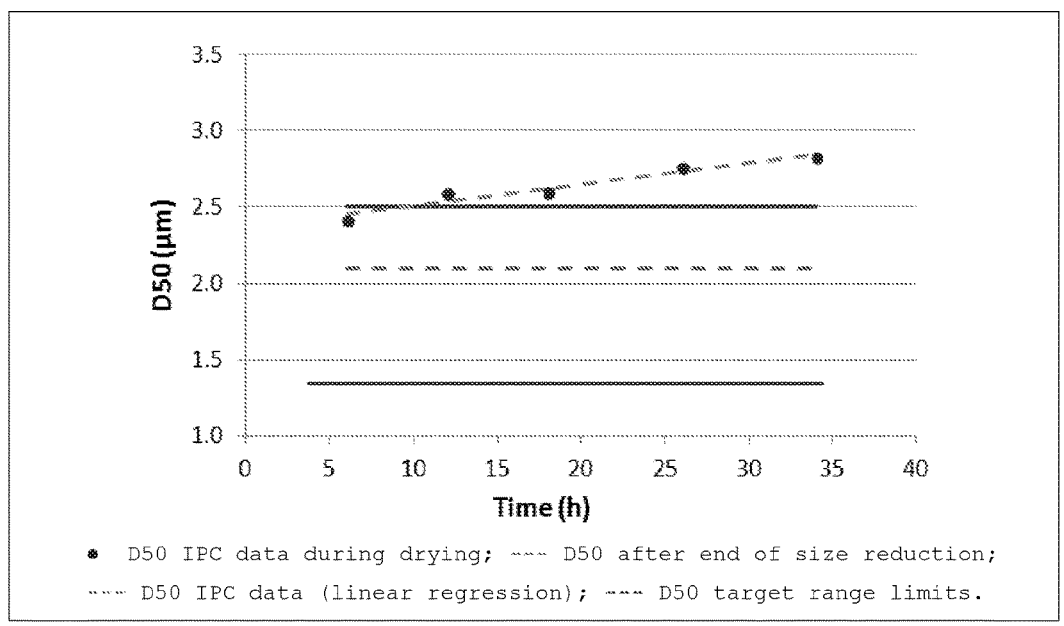
Figure 2 – In-Process Control data during drying of a MFM batch after HPH

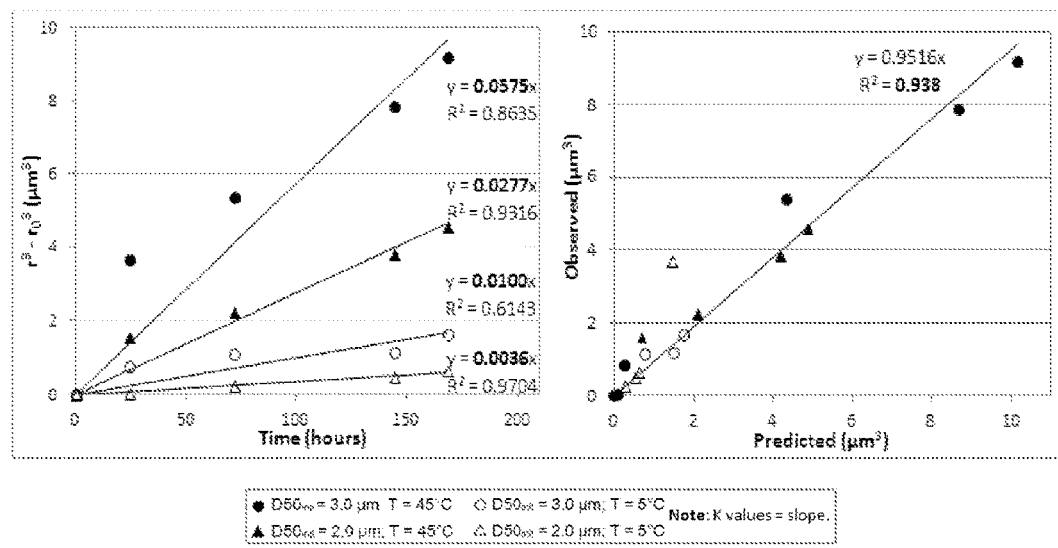
Figure 3 - Theoretical OR model versus experimental data (left plot) and observed versus predicted results (right plot)

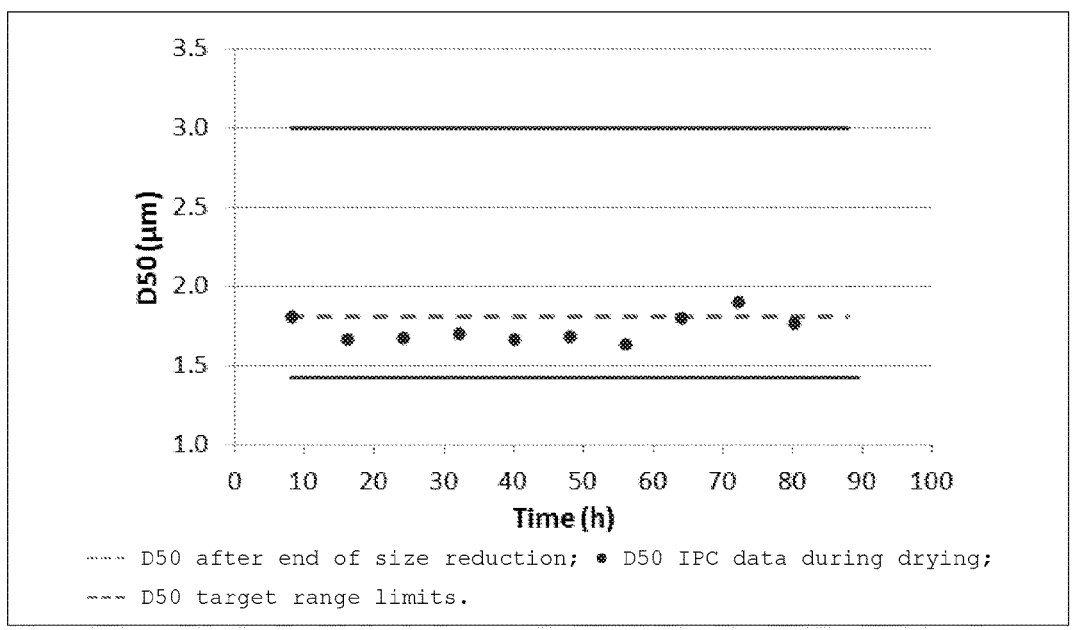
Figure 4 - In-Process Control data during drying of a MFM batch using DSD

DYNAMIC SUSPENSION DRYING (DSD) TO CONTROL OSTWALD RIPENING

FIELD OF THE INVENTION

The present invention relates to a process for the control of the Ostwald Ripening phenomenon occurring in particle suspensions without the need for addition of stabilizing agents, by using high pressure homogenization under mild conditions in a way that no increase or decrease in particle size occurs, thus allowing the stabilization of the suspension during the isolation step in the form of a dried powder.

BACKGROUND OF THE INVENTION

Ostwald Ripening Phenomenon

Ostwald ripening (Rawlins 1982; Muller & Bohm 1998) has been described for ultrafine dispersed systems and is responsible for crystal growth, thus increasing the mean diameter of the particle size distribution (PSD). Ostwald ripening is caused by the differences in dissolution solubility between small and large particles. It is in practice an effect based on the higher saturation solubility of very small particles as compared to larger ones. Molecules diffuse from the higher concentrated area around small particles (higher saturation solubility) to areas around larger particles possessing a lower drug concentration. This leads to the formation of a supersaturated solution around the large particles and consequently to drug crystallization and growth of the large particles. The diffusion process of the drug from the small particles to the large particles leaves an area around the small particles that is not saturated any more, consequently leading to dissolution of the drug from the small particles and finally complete disappearance of the small particles. (V. B. Patravale, 2004)

Importance of Ostwald Ripening Phenomenon Control

The presence of this phenomenon, that causes an increase in the mean diameter of the particle size distribution over time, results in an instable behavior of a suspension; therefore, during drying of the suspension (in order to isolate the dry powder), particle size distribution will also tend to shift and, as a consequence, may affect the bioavailability, toxicity and efficacy of the final product.

Current Strategies to Prevent Ostwald Ripening Phenomenon

Typical ways of preventing Ostwald Ripening in suspensions include the addition of stabilizing agents to the original suspension.

WO 2008/013785 discloses a process to stabilize suspensions of solid particles of docetaxel in an aqueous medium using an oil in water emulsion process, where proteins or other polymers are applied as surfactants. The prepared dispersion exhibited little or no particle growth after formation that resulted from Ostwald Ripening. In this document a non-polymeric hydrophobic compound which is substantially insoluble in water is used as an Ostwald Ripening inhibitor.

U.S. Pat. No. 6,749,868 and WO 98/14174 disclose a process to stabilize suspensions of solid particles of paclitaxel by coating them with a protein (that acts like a stabilizing agent) in the absence of conventional surfactants to obtain a stable active pharmaceutical ingredient (API) dispersion with low particle size distributions.

Another example is the usage of three surfactants poloxamer 188: Tween®80 and glycerol used in two different concentrations to stabilize tarazepide particles after homogenization using a wet milling lab scale unit. Stability of the nanosuspensions was found for at least a quarter of a year within an acceptable range and did not change very much within 91 days. (C. Jacobs, 2000)

Additionally US Publication No. 2005/009908 refers to a process for preventing Ostwald Ripening (OR) in particles (particularly in the sub-micron range) in an aqueous medium. This process comprises two steps to produce a stable suspension:

a) Producing a solution of a substantially water insoluble API and an inhibitor in a water miscible organic solvent;

b) Addition of an aqueous phase, comprising water and a stabilizer, precipitating solid particles comprising the inhibitor and the API.

In this document, the controlled precipitation and the presence of the stabilizing agent are claimed to prevent Ostwald Ripening phenomena in the aqueous medium.

However, stabilizing agents need to be carefully selected in order to assure the desired Ostwald Ripening control. For example ascorbyl palmitate nanocrystals stabilized with Tween® 80 remained in the nanometer size during 3 months of storage at three different temperatures as, on the other hand, this effect was not observed when using sodium dodexyl sulfate (SDS) to stabilize the same particle nanosuspensions. (V. Teeranachaideekul, 2008). Additionally, using these stabilizing agents may not be desirable and/or feasible in all cases; for example, there is a reduced number of excipients approved for inhalation delivery and, even if approved, their addition can impact the aerodynamic performance of the particles, thus affecting the product performance. Based on the earlier approaches that can control Ostwald Ripening without requiring further addition of stabilization agents would be advantageous.

Theoretically particle growth caused by Ostwald Ripening could be eliminated, without the need of stabilization agents, if all the particles in the dispersion had the same size (unimodal distribution) thus improving homogeneity of the particles population (Cornelia M. Keck, et all, 2006); such can be further potentiated by combining this with low solubility of the drug in the anti-solvent, this way keeping the concentration differences sufficiently low to avoid the ripening effect (R. H. Muller, et all, 2001).

U.S. Pat. No. 4,826,689 describes a process to prepare particles with a uniform particle size distribution. This process is carried out by infusing an aqueous precipitating liquid into a solution of the solid in an organic liquid under controlled conditions of temperature and infusion rate, thus controlling the particle size. U.S. Pat. No. 4,997,454 describes a similar process, in which an aqueous or non-aqueous solution is used as a precipitating liquid.

However, in both the earlier cases, the need to isolate the particles as soon as they are produced is mentioned, in order to minimize any particle growth (which may be indicative of the impracticability of true monodisperse distributions and/or of the unavoidable effect of residual solubility). Therefore, in processes which use suspensions in wet media to reduce particle size and which require long residence times, particle growth in the anti-solvent becomes difficult to control or even inevitable.

So far no strategies are reported which are capable of stabilizing the particle size in the presence of Ostwald Ripening without involving immediate isolation of the powder and/or the use of stabilization agents. We have appreciated that it would be desirable to improve on this situation, and have now devised a method which is capable of stabilizing the particle size in the presence of Ostwald Ripening phenomena without any stabilizing agent and without the need to immediately isolate the particles in the form of a powder.

BRIEF DESCRIPTION OF THE INVENTION

Accordingly the present invention provides a method for processing particles of a pharmaceutical ingredient in suspension comprising the steps of:
 a) Reducing the size of the pharmaceutical ingredient particles in the suspension under high pressure conditions by using a high pressure homogenization apparatus;
 b) Isolating the particles from the suspension in the form of a powder, characterized in that during the isolation step at least a part of the suspension is recycled to the high pressure homogenization apparatus at mild pressure conditions.

Preferably, the recycling is performed continuously.

Accordingly the present invention further provides particles obtained by a method referred above.

Accordingly the present invention further provides a pharmaceutical formulation comprising the particles obtained by the method referred above.

Accordingly the present invention further provides an apparatus for processing particles of a pharmaceutical ingredient in suspension comprising:
 (1) a feed vessel for forming a suspension of the pharmaceutical ingredient and an anti-solvent;
 (2) a high pressure homogenization apparatus which is capable of operating in a recirculation mode for obtaining a desired particle size;
 (3) a suspension drying device for isolating the particles in the form of a dry powder, wherein the apparatus is configured such that during the step of isolation of particles at least a part of the suspension is recycled to the high pressure homogenization apparatus at mild pressure conditions.

Preferably, the suspension is homogenous. And, preferably the recycling is performed continuously. The recycling substantially minimizes or prevents Ostwald Ripening in the suspension.

Preferably, the high pressure homogenization apparatus comprises a gap valve, rotor stator, ultrasonic, homogenization cell and high sheer fluid processing unit.

Preferably, the suspension drying device comprises a device for carrying of a drying process such as spray drying, lyophilization, evaporation to dryness and a fluid bed drying step.

The present invention further provides a method of preventing Ostwald Ripening in a process of obtaining particles of a pharmaceutical ingredient in powder form from a suspension of the pharmaceutical ingredient using a high pressure homogenization process, wherein the said method comprises recycling at least a part of the suspension at mild pressure conditions during the step of isolation of the particles from the suspension.

The present invention further provides the use, in a process of obtaining particles of a pharmaceutical ingredient in powder form from a suspension of the pharmaceutical ingredient using a high pressure homogenization process, of the step of recycling at least a part of the suspension at mild pressure conditions during the step of isolation of the particles from the suspension to prevent Ostwald Ripening. We call this technology dynamic suspension drying (DSD).

In the above method and use, preferably the recycling is performed continuously.

BRIEF DESCRIPTION OF THE DRAWINGS

FIG. 1 is a schematic representation of the dynamic processing of the particles according to the present invention;
FIG. 2 shows in-process control data during drying of a mometasone furoate monohydrate (MFM) batch after high pressure homogenization (HPH).
FIG. 3 shows theoretical Ostwald Ripening (OR) model versus experimental data (left plot) ad observed versus predicted results;
FIG. 4 shows in-process control data during drying of a MFM batch using DSD.

DETAILED DESCRIPTION OF THE INVENTION

The present invention relates to a process for controlling Ostwald Ripening phenomenon in particle suspensions using high pressure homogenization (HPH) at optimized mild pressure conditions.

This process controls Ostwald Ripening in solid dispersions without the addition of stabilizing agents and/or the need for immediate powder isolation.

High pressure homogenization requires the pharmaceutical ingredient to be suspended in an anti-solvent. In practice, products suspended will frequently exhibit residual solubilization, even using the most appropriate anti-solvents is hard to avoid residual solubilization. Therefore, the pharmaceutical ingredient will be vulnerable to particle size instability phenomena namely Ostwald Ripening. Thus, this process is applicable to any pharmaceutical ingredient that suffers from this phenomenon when suspended in an anti-solvent.

This process is an inventive procedure where the solid pharmaceutical ingredient, suspended in an anti-solvent, after being processed by HPH at elevated pressure (and particle size distribution has plateaued at target values), is isolated in the form of a dried powder while recycling, preferably continuously, at least a part of the suspension to the HPH unit at optimized mild pressure conditions.

These mild conditions need to be carefully selected in so that:
 a) Any increase in particle size due to Ostwald Ripening is prevented through the stabilization effect of the recirculation procedure and subsequent HPH at mild pressure conditions;
 b) Further reduction in particle size does not occur, because only particle growth is being prevented at mild conditions.

Through this delicate balance (neither growth nor reduction of particle size), stabilization of the suspension is accomplished without the need for addition of stabilizing agents. This procedure allows for the pharmaceutical ingredient to be isolated in the absence of increasing particle size trends, without any constraints regarding the time window in which the isolation step needs to be completed.

Since there is no need to add to the suspension any stabilizing agents (excipients), testing for determination of compatibility of excipients with other excipients, between excipients and the anti-solvent or between excipients and an active pharmaceutical ingredient becomes irrelevant, because the material is manufactured solely in association with the suspending solvent needed for the processing. This offers a substantial advantage over previously reported approaches, because it is a much simpler and effective process and, without the need for stabilizing agents, there will be no impacting on the drug product performance (e.g., stability, bioavailability) or manufacturability.

The present invention further provides high reproducibility over the isolation of the pharmaceutical ingredient, keeping the particle size distribution stable. Another advantageous feature is that the process herein disclosed does not change the polymorphic form of the pharmaceutical ingredient, aiming only at solving the problem of particle growth caused by Ostwald Ripening phenomenon. Furthermore, the disclosed invention can be easily scaled up and is, therefore, feasible at any manufacturing scale.

FIG. 1 shows an apparatus for dynamic processing of the particles according to the present invention. The apparatus comprises a high pressure homogenization apparatus (1), a feed vessel (2) and a suspension drying device (3).

Within the feed vessel (2) the pharmaceutical ingredient is suspended in an anti-solvent and stirred in order to obtain a preferably homogeneous suspension. The homogeneous suspension is then fed to a HPH apparatus (1) operating at elevated pressures in recirculation mode (returning the discharge of the HPH to the feed vessel (2) inlet) to obtain a desired particle size.

After the homogenization step described above, and after reaching the desired particle size, at least a part of the suspension is fed to a drying device (3) in order to isolate the pharmaceutical ingredient in the form of a powder. Preferably, the lower limit of the amount of the part of the suspension which is being recycled is about 200 ml.

Throughout this isolating step, at least a part of the suspension is recycled, preferably continuously, to the HPH (1) unit (returning the discharge of the HPH to the stirred vessel inlet) at optimized mild pressure conditions allowing for the pharmaceutical ingredient to be isolated in the absence of increasing particle size trends and without any constraints regarding the time period during which the isolation step needs to be completed.

Definitions high pressure homogenization (HPH) is a fluid mechanical process that involves the subdivision of particles in suspension into micron sizes.

The high pressure homogenization step may be carried out in any suitable kind of high pressure homogenizer, namely those available in the market employing homogenization technologies such as, gap valve, rotor stator, ultrasonic, homogenization cell, high sheer fluid processing or similar devices manufactured by for example Niro, Microfluidics, DeBee and others.

High pressure can be defined as a homogenization pressure of typically from about 500 to about 3500 bar—applied to reduce the particle size to target.

Mild pressure conditions are here defined as any pressure conditions below the previously applied high pressure conditions (that were used to reduce the particle size), capable of producing the desired suspension stabilization effect (preventing increases in particle size) without any further particle size reduction. The skilled person will be able to establish the optimum mild pressure easily using a few routine experiments, because an increase or decrease in the particle size can be monitored.

Suitably, mild pressure conditions refer to a pressure lower than the previously applied process pressure (applied to reduce the particle size), preferably pressures of less than 500 bar.

The isolation step, as defined herein, comprises the entire process of isolating and drying the particles from the suspension, once the chosen particle size has been achieved. This may be accomplished by any drying technique known in the art which is capable of forming the pharmaceutical ingredient as a dry powder. Preferred drying techniques may comprise: evaporation to dryness, lyophilization, spray drying, fluid bed drying, etc.

The pharmaceutical ingredient may be any kind of active pharmaceutical ingredient or excipient that suffers from Ostwald Ripening when in suspension with an anti-solvent.

An anti-solvent is a media where the pharmaceutical ingredient shows none or low solubility resulting in the dispersion of the solid pharmaceutical ingredient. Examples of suitable antisolvents that are typically used are methanol, ethanol, acetone, ethyl acetate, n-heptane or water.

The following example uses mometasone furoate monohydrate as a model drug and by no means limits the scope of the invention.

EXAMPLE 1

1. Mometasone furoate monohydrate (2330 g) was suspended in water (23000 g) and stirred for 5 hours in order to obtain a uniform suspension; afterwards, it was fed to a lab scale HPH apparatus operating at pressures ranging from 757.5 to 1363.5 bar in recirculation mode (returning the discharge of the HPH to the stirred vessel inlet), having this step ended with a Dv50~2 μm after 63 hours of operation;

2. After the homogenization step described in point 1. above, particle size of the active pharmaceutical ingredient was within target and the suspension was fed to a lab scale spray dryer in order to isolate the active pharmaceutical ingredient in the form of a powder;

3. Throughout the subsequent isolating step (during which the suspension was kept under stirring in a feed vessel), increasing values of particle size were observed over time, as shown in FIG. 2. Due to this unstable behavior (the final material properties were trending out of targets) the batch had to be interrupted to accommodate an investigation.

4. In order to confirm that the observed PS instability was being caused by OR phenomenon, a laboratory study was designed. In this study, two suspensions of MFM were size-reduced via HPH to a different PS (D50=2.0 μm and 3.0 μm) and, afterwards, stored at different temperatures (5° C. and 45° C.). In all cases, PS growth was monitored by considering five sampling time points (24, 72, 144 and 168 h).

Before fitting the obtained data, a literature review was conducted; several models can be found for OR modeling, with most of them being modifications of the Lifshitz, Slyozov and Wagner (LSW) theory (Eq. 1), which is a kinetic model that translates an isothermal variation of the more general problem (M. Mrotzek, 2008):

$$\bar{r}^N = \bar{r}_0^N + Kt \text{ with } K = \frac{8\gamma V_m^2 D_m C_{(\infty)}}{9RT} \tag{Eq. 1}$$

where $\bar{r}$ is the average radius of the particle (μm), $\bar{r}_0$ is the radius of the particle at t=0, K is a constant that varies with T (absolute temperature), t is time, γ is the interfacial tension, $V_m$ is the molar volume of the dispersed phase, $C_{(\infty)}$ is the bulk solubility of the dispersed phase, $D_m$ is the molecular diffusion coefficient, R is the universal gas constant; additionally, N is an exponent that assumes the value of 3 or 2, depending on diffusion or agglomeration being the limiting step (E. Lee, 2006).

Based on the above equation, two important observations (M. Mrotzek, 2008) (V. Sadtler, 2002) are expected when in the presence of OR: i) a cubic or quadratic growth (depending on the limiting step) and ii) a more pronounced increase of K for higher temperatures. As shown in FIG. 2 (left plot), both previous observations are valid for the current case-study, thus supporting the presence of OR; in this plot, $r^3-r_0^3$ was represented as a function of time and the K value determined by performing a linear regression where Eq. 1 was assumed as the theoretical model; as shown in FIG. 3 (right plot) a good correlation coefficient was obtained ($R^2$=0.94).

Overall, the results show a significant decrease of the phenomenon when temperature is decreased (due to its effect on solubility), as K values are more than five times lower for 5° C., when compared to 45° C. However, for the target range of D50 (~2 μm), OR is still significant at 5° C. and lower temperatures would not be feasible due to the necessary use of water as process anti-solvent.

5. Regarding the data obtained in point 4. above, the root cause for the particle size trend was found to rely on the unstable behavior of the suspension due to Ostwald Ripening phenomenon;

6. In order to move forward with the manufacturing of the mentioned batch and following ones, the dynamic suspension drying (DSD) was applied targeting the stabilization of the suspension during drying for that purpose the suspension was recycled at a moderated pressure of 455 bar. The analytical data obtained from applying the DSD procedure is shown in FIG. 4.;

7. The isolated product manufactured through the DSD configuration showed a particle size distribution very similar to the one obtained at the end of the HPH step (Dv50~2 μm on average), thus demonstrating the efficacy of this approach in preventing Ostwald Ripening.

8. The crystalline form was kept unchanged, as confirmed by XRPD analysis.

9. Through this delicate balance, stabilization of the suspension is accomplished (FIG. 3) in a simpler, effective, reproducible and easily scalable way; additionally, no impact on the polymorphic form was noticeable by XPRD analysis.

The invention claimed is:

1. A method for processing particles of a pharmaceutical ingredient in suspension comprising the steps of:
   a) reducing the particle size of the pharmaceutical ingredient in the suspension under high pressure conditions by using a high pressure homogenization apparatus, wherein the suspension is formed by adding the pharmaceutical ingredient to an anti-solvent, which is any media where the pharmaceutical ingredient shows none or low solubility; and
   b) isolating the particles from the suspension in the form of a powder, characterized in that during the isolation step at least a portion of the suspension is recycled to the high pressure homogenization apparatus under mild pressure conditions.

2. The method according to claim 1 wherein the high pressure condition is a pressure in the range of from 500 to 3500 bar.

3. The method according to claim 1 wherein the mild pressure condition is a pressure lower than the high pressure applied to the particle size reduction.

4. The method according to claim 2, wherein the mild pressure condition is below 500 bar.

5. The method according to claim 1 wherein the high pressure homogenization apparatus comprises gap valve, rotor stator, ultrasonic, homogenization cell or high sheer fluid processing.

6. The method according to claim 1 wherein the particle isolation step comprises a drying process for obtaining the particles in the form of a dry powder.

7. The method according to claim 6 wherein the drying process comprises spray drying, lyophilization, evaporation to dryness or a fluid bed drying step.

8. The method according to claim 7 wherein the drying step is a spray drying process.

9. The method according to claim 1 wherein the anti-solvent is methanol, ethanol, acetone, ethyl acetate, n-heptane or water.

10. The method according to claim 1 wherein the suspension is continuously recycled to the high pressure homogenization apparatus at optimized mild pressure conditions.

11. The method according to claim 1 wherein the suspension does not contain a stabilizing agent or a surfactant.

12. The method according to claim 1 wherein there are no time constraints regarding completion of the particle isolation step.

13. The method according to claim 1 wherein the particle size is stabilized during the pharmaceutical ingredient isolation step.

14. A method of minimizing Ostwald Ripening in a process for producing powder particles of a pharmaceutical ingredient from a suspension of said pharmaceutical ingredient, wherein said process comprises the steps of:
   a) reducing the particle size of the pharmaceutical ingredient in the suspension under high pressure conditions by using a high-pressure homogenization apparatus, wherein the suspension is formed by adding the pharmaceutical ingredient to an anti-solvent, which is any medium where the pharmaceutical ingredient shows none or low solubility; and
   b) isolating the particles from the suspension in the form of a powder, characterized in that during the isolation step, at least a portion of the suspension is recycled to the high-pressure homogenization apparatus under mild pressure conditions.

15. A method for processing particles of a pharmaceutical ingredient in suspension comprising the steps of:
   a) reducing the particle size of the pharmaceutical ingredient in the suspension under high pressure conditions by using a high pressure homogenization apparatus, wherein the suspension is formed by adding the pharmaceutical ingredient to an anti-solvent, which is any media where the pharmaceutical ingredient shows none or low solubility, such as methanol, ethanol, acetone, ethyl acetate, n-heptane or water; and
   b) isolating the particles from the suspension in the form of a powder, characterized in that during the isolation step at least a portion of the suspension is recycled to the high pressure homogenization apparatus under mild pressure conditions.

* * * * *